United States Patent [19]

Burrus et al.

[11] 4,180,687

[45] Dec. 25, 1979

[54] REACTION OF FORMALDEHYDE IN BUTYNEDIOL

[75] Inventors: Harry O. Burrus; Donald I. Garnett, both of Wilmington, Del.

[73] Assignee: E. I. Du Pont de Nemours and Company, Wilmington, Del.

[21] Appl. No.: 899,297

[22] Filed: Apr. 24, 1978

[51] Int. Cl.² .................. C07C 29/24; C07C 33/04
[52] U.S. Cl. .................................... 568/856; 568/855
[58] Field of Search .............................. 568/856, 855

[56] References Cited

U.S. PATENT DOCUMENTS

| | | | |
|---|---|---|---|
| 2,993,078 | 7/1961 | Hort | 568/856 |
| 3,129,252 | 4/1964 | Graham et al. | 568/856 |
| 3,130,236 | 4/1964 | Shull | 568/856 |
| 3,232,996 | 2/1966 | Graham et al. | 568/856 |

*Primary Examiner*—Joseph E. Evans

[57] ABSTRACT

Formaldehyde in crude BYD, can be reacted to a polymeric substance in the presence of NaOH or $Na_2CO_3$ at high temperatures.

6 Claims, No Drawings

REACTION OF FORMALDEHYDE IN BUTYNEDIOL

TECHNICAL FIELD

This invention relates to the production of butynediol (BYD) for use in the manufacture of tetrahydrofuran.

BACKGROUND ART

It is well known that tetrahydrofuran can be produced by a series of reactions starting with the reaction of aqueous formaldehyde and acetylene in the presence of a catalyst, i.e., copper acetylide complex, to form butynediol. Butynediol is then reduced by hydrogenation to butanediol. Butanediol is cyclized in the presence of sulfuric acid to tetrahydrofuran.

Some commercial processes for the synthesis of butynediol (see U.S. Pat. No. 3,560,576) operate with excess formaldehyde, thereby improving yields. However, as formaldehyde inhibits the reduction of BYD in the hydrogenation step, it is necessary to remove formaldehyde from butynediol. Generally, the crude butynediol is distilled to remove formaldehyde which is recycled in the system. This distillation step is expensive both in the initial cost of equipment and in energy consumption during use.

DISCLOSURE OF INVENTION

It has now been found that the distillation or other separation step may be eliminated entirely. Instead, the crude butynediol is subjected to high temperatures and treated with alkali metal hydroxides or carbonates, thereby converting the formaldehyde to polymeric materials, presumably high molecular weight aldehyde resins, which are not detrimental to the reduction of BYD.

Butynediol is commercially synthesized by the reaction of acetylene and formaldehyde in the presence of a catalyst. Generally, the reaction is carried out in the liquid phase in the presence of solvents or diluents such as water. The reaction is carried out at a weakly acid or neutral pH. As the reaction proceeds, it produces formic acid and basic buffers are added to the system to control pH. In general, the crude BYD leaving the reactor may be characterized as a weakly acid, or neutral aqueous solution containing BYD, unreacted formaldehyde, and small amounts of impurities from side reactions such as methanol and propargyl alcohol.

The formaldehyde concentration in the liquid in contact with the catalyst during the reaction may be as high as 66 weight percent but more commonly is 1–10 weight percent under steady state conditions. Some butyndiol production facilities are operated without excess formaldehyde and therefore only trace quantities of formaldehyde exist in the product. The present invention is technically operative in removing trace quantities of formaldehyde but there is little economic incentive to do so. By the same token, if more than 10 weight percent of excess formaldehyde is present in the butyndiol, it is more economical to distill the product and recycle the formaldehyde. Of course, the economic considerations are based on the cost of energy and formaldehyde and are therefore subject to change. In the range of 0.5 to 10 weight percent excess formaldehyde it becomes economically attractive to react the formaldehyde to a polymeric material which is not harmful to the reduction of BYD. It is more preferable to use the process of the invention when the excess formaldehyde is in the range of 1.0 to 5.0 weight percent. Obviously the lower the amount of excess formaldehyde in the BYD, the more economically attractive the system from the standpoint of cost of formaldehyde and treating material. However, as the amount of excess formaldehyde is decreased, the rate of formation of BYD is decreased unless operating changes are made to compensate. At some point operating changes are not sufficient to compensate and therefore some excess formaldehyde is preferred.

To prevent the excess formaldehyde in BYD from inhibiting the reduction by hydrogenation, an alkali metal hydroxide or carbonate is added. Of the alkali metals, sodium is preferred because of its low cost. Although the mechanism of the reaction is not entirely understood, it is believed that the hydroxide or carbonate acts as a catalyst in converting the formaldehyde to a polymeric material. This polymeric material passes through the hydrogenation step without inhibiting the reaction.

The preferred catalysts, sodium hydroxide or sodium carbonate may be characterized as basic materials which are soluble in aqueous BYD and are not detrimental to the reduction by hydrogenation of BYD.

The amount of catalyst should be from 0.05 to 1.0 mols catalyst/mol formaldehyde. The lower limit is set to ensure that the reaction proceeds at a reasonable rate. The upper limit ensures a rapid rate of reaction and although more catalyst may be used, no particular benefit is achieved thereby. The preferred range of 0.1 to 0.5 mols catalyst/mol formaldehyde provides a rapid reaction.

The catalyst may be contacted with the crude BYD by any known method. Since the reaction proceeds rapidly, in a matter of minutes, long hold-up time is not required. An advantage of this invention is that it can be easily incorporated into an existing butynediol production facility. The catalyst can be injected directly into the crude BYD pipeline. Mixing would be provided by the turbulence in the pipeline. To attain the proper temperature, the crude butynediol could be sent to a small heated pot, capable of providing a two-minute residence time.

A critical facet of the catalytic reaction is temperature. The crude BYD and catalyst is preferably raised to a temperature of 140° to 180° C. to ensure reaction. At lower temperatures the catalytic reaction proceeds slowly and direct chemical reactions use up the catalyst. At higher temperatures, some hazard may be incurred by the degradation of BYD and byproduct reactions are likely to occur. More preferably the temperature is maintained at 155°–170° C.

The reaction is not pressure dependent and the autogenous pressure of the system is adequate.

BEST MODE

Catalytic Reaction Procedure

A 500 ml solution, containing approximately 53% $H_2O$, 44% BYD, and 3% HCHO was charged to a 1 liter autoclave with mechanical stirrer. The autoclave was flushed with nitrogen to remove air and then heated to 165° C. At time 0 the stated amount of catalyst was charged to the system. After 1 minute a sample was withdrawn from the autoclave and tested by polarograph for % HCHO. Samples were tested using decreasing amounts of sodium carbonate as shown below.

TABLE I

| | Catalytic Reaction of Formaldehyde | | |
|---|---|---|---|
| | $Na_2CO_3$/HCHO | | |
| Example | g/g | mols/mol | % HCHO |
| 1 | 53/15 | 1.00 | <0.1 |
| 2 | 27/15 | 0.50 | <0.1 |
| 3 | 13/15 | 0.25 | <0.1 |
| 4 | 7/15 | 0.12 | <0.1 |

From the test results, the reaction of sodium carbonate and formaldehyde appears to be catalytic as less than stoichiometric quantities of sodium carbonate may be used. The results also indicate that formaldehyde is removed from the butynediol solutions. It is believed that the formaldehyde is converted to a polymeric material.

To observe the effect of converting the formaldehyde in butynediol on the subsequent hydrogenation of butynediol, a series of hydrogenation experiments were performed.

Hydrogenation Procedure

The equipment consisted of a 300 cc Autoclave Engineers magnetically stirred autoclave, a Lapp Pulsafeeder ® pump and a strip chart temperature recorder. The clave was charged with 50 cc of distilled water and 5 g Grace No. 28 Raney active nickel (weighed damp), from which all the available aluminum had been removed by caustic leaching. (The catalyst was purchased in its active state).

The clave was sealed and heated with constant stirring to 100° C., pressurized to 1000 psig hydrogen pressure, and 100 cc of sample was added to the clave at 1.0 cc/min. The temperature control system of the autoclave maintained the reaction temperature at 100° C. even though the hydrogenation is exothermic. At the end of the addition, the reaction mixture was stirred an additional 15 minutes, cooled rapidly and the catalyst removed by filtration. Product analysis was done by flame ionization gas chromatography, using a 20'×⅛" SS Carbowax 20 m on Chromosorb W column.

Using the above procedure, the following samples were tested.

Standard—A sample obtained from a commercial facility which analyzed as 47.4% butynediol, 52.4% water and 0.2% formaldehyde.

Sample A—To the above described Standard sample was added 3.0% formaldehyde resulting in a sample which analyzed as 44.1% butynediol, 52.4% water and 3.5% formaldehyde.

Solution B—Sample A was laboratory-treated with 2.5 g NaOH pellets dissolved in 25 cc water at 165° C., held for five minutes and then neutralized to pH 7 with $H_2SO_4$.

Solution C—Sample A was laboratory-treated with 1.2 g NaOH pellets dissolved in 25 cc water at 165° C., held for five minutes and then neutralized to pH 7 with $H_2SO_4$.

TABLE II

HYDROGENATION OF PRODUCT FORMALDEHYDE REACTION TESTS

| Sample | g NaOH added to Sample | g NaOH / g HCHO | mols NaOH / mols HCHO |
|---|---|---|---|
| Standard | 0 | 0 | 0 |
| "A" | 0 | 0 | 0 |
| "B" | 2.5 | 0.28 | 0.21 |
| "C" | 1.2 | 0.14 | 0.10 |

| Sample | Minutes | % HCHO by Polarograph | % BAD After Hydrogenation |
|---|---|---|---|
| Standard | 0 | 0.2* | 98.4 |
| "A" | 0 | 3.54** | 65.7 |
| "B" | 0 | 3.09 | |
| | 1 | <0.02 | |
| | 2 | — | 97.2 |
| | 5 | — | |
| "C" | 1 | 0.03 | |
| | 2 | — | 96.3 |
| | 5 | — | |

*Wet Analysis
**All NaOH/HCHO calculations based on 3.54 wt % HCHO in 250 ml stock solution.

As is seen by the above experiments, sodium hydroxide is a suitable catalyst for this reaction. Furthermore, neither the catalyst nor the polymeric materials (reacted formaldehyde) are injurious to the hydrogenation of butynediol.

We claim:

1. In a process for the production of crude butynediol containing 0.5–10 weight percent of formaldehyde by the reaction of aqueous formaldehyde and acetylene in the presence of a cuprous acetylide complex the improvement comprising reacting the formaldehyde in the crude butynediol with 0.05 to 1.0 mols of alkali metal hydroxide or carbonate per mol of formaldehyde at a temperature of 140° to 180° C. for a period of time until the formaldehyde is converted into a polymeric substance.

2. The process of claim 1 wherein the alkali metal is sodium.

3. The process of claim 1 wherein the temperature is 155°–170° C.

4. The process of claim 1 wherein the catalyst is present in an amount of 0.1 to 0.5 mols catalyst/mol of formaldehyde.

5. The process of claim 1 wherein the formaldehyde in the crude butynediol is 1.0 to 5.0 weight percent.

6. The process of claim 1 wherein the period of time is up to five minutes.

* * * * *